United States Patent
Kondo et al.

(10) Patent No.: US 10,210,309 B2
(45) Date of Patent: Feb. 19, 2019

(54) IMAGE DISPLAY METHOD, MEDICAL DIAGNOSTIC IMAGING APPARATUS, AND MEDICAL IMAGE PROCESSING APPARATUS

(75) Inventors: Takashi Kondo, Tochigi (JP); Hiromasa Yamagishi, Tochigi (JP); Teruhiko Ebina, Tochigi (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1173 days.

(21) Appl. No.: 12/688,329

(22) Filed: Jan. 15, 2010

(65) Prior Publication Data

US 2010/0183208 A1 Jul. 22, 2010

(30) Foreign Application Priority Data

Jan. 21, 2009 (JP) ................................. 2009-011301

(51) Int. Cl.
*G06K 9/00* (2006.01)
*G06F 19/00* (2018.01)

(52) U.S. Cl.
CPC .................. *G06F 19/321* (2013.01)

(58) Field of Classification Search
CPC ......... A61B 5/055; A61B 6/032; A61B 6/463; A61B 6/502; A61B 6/461; G06F 19/321; G06F 19/323; G06F 2201/835; G06F 21/6245; G06F 19/324; G06T 2210/08; G06T 2207/20092; G06T 2210/41; G16H 10/60
USPC .......... 382/128, 305, 2, 3; 386/95, 125, 241; 705/2, 3; 345/158, 619, 98, 424, 690; 600/400, 407; 238/128, 131
See application file for complete search history.

(56) References Cited

U.S. PATENT DOCUMENTS

| | | | | |
|---|---|---|---|---|
| 4,768,099 A | * | 8/1988 | Mukai | ........................... 358/403 |
| 5,293,313 A | * | 3/1994 | Cecil | ..................... G06F 19/321 |
| | | | | 345/690 |
| 5,452,416 A | * | 9/1995 | Hilton | .................... G06F 19/321 |
| | | | | 345/424 |
| 5,991,760 A | * | 11/1999 | Gauvin et al. | |
| 6,067,075 A | * | 5/2000 | Pelanek | ........................ 345/158 |
| 6,081,267 A | * | 6/2000 | Stockham | .............. G06F 19/321 |
| | | | | 378/98 |
| 6,614,453 B1 | * | 9/2003 | Suri | ....................... G06F 19/321 |
| | | | | 345/419 |
| 6,847,697 B2 | * | 1/2005 | Kurahashi | ........................ 378/62 |

(Continued)

FOREIGN PATENT DOCUMENTS

JP 7-105067 4/1995

*Primary Examiner* — Victoria P Shumate
*Assistant Examiner* — Teresa S Williams
(74) *Attorney, Agent, or Firm* — Oblon, McClelland, Maier & Neustadt, L.L.P.

(57) ABSTRACT

Setting information in which a sequence with medical meaning is set as the sequence of viewing a plurality of medical image data is read from a portable medium. Moreover, in accordance with the sequence set in the setting information, a plurality of medical image data stored in the portable medium is replicated into a storage unit of a terminal device as replicated medical image data. Furthermore, before replication of all of the medical image data stored in the portable medium is finished, reception of an output instruction is started. Replicated medical image data corresponding to medical image data specified in the output instruction is then output to an output unit.

16 Claims, 8 Drawing Sheets

(56) References Cited

U.S. PATENT DOCUMENTS

| | | | |
|---|---|---|---|
| 6,925,319 B2* | 8/2005 | McKinnon | 600/407 |
| 6,954,767 B1* | 10/2005 | Kanada | |
| 6,954,802 B2* | 10/2005 | Sutherland et al. | 710/5 |
| 7,057,751 B1* | 6/2006 | Shiraiwa | 358/1.15 |
| 7,302,164 B2* | 11/2007 | Wright et al. | 386/225 |
| 7,556,725 B2* | 7/2009 | Mayes | H01L 22/00 204/400 |
| 7,801,965 B2* | 9/2010 | Hofmann et al. | 709/211 |
| 8,086,077 B2* | 12/2011 | Eichhorn | G06F 17/3028 382/240 |
| 8,140,481 B2* | 3/2012 | Sato et al. | 707/653 |
| 8,233,750 B2* | 7/2012 | Minakuchi et al. | 382/305 |
| 8,303,505 B2* | 11/2012 | Webler et al. | 600/447 |
| 8,376,947 B2* | 2/2013 | Rambod et al. | 600/437 |
| 8,483,550 B2* | 7/2013 | Wright et al. | 386/344 |
| 2003/0123719 A1* | 7/2003 | Kurahashi | 382/131 |
| 2004/0015079 A1* | 1/2004 | Berger et al. | 600/437 |
| 2004/0044666 A1* | 3/2004 | Piehler | 707/10 |
| 2005/0240445 A1* | 10/2005 | Sutherland | G06F 19/321 705/3 |
| 2006/0093207 A1* | 5/2006 | Reicher | G06F 19/321 382/156 |
| 2006/0095423 A1* | 5/2006 | Reicher | G06F 19/327 |
| 2006/0122482 A1* | 6/2006 | Mariotti et al. | 600/407 |
| 2006/0149601 A1* | 7/2006 | Langhofer et al. | 705/3 |
| 2006/0177114 A1* | 8/2006 | Tongdee | G06F 17/30265 382/128 |
| 2006/0182324 A1* | 8/2006 | Motoki | G06F 17/3028 382/128 |
| 2006/0230072 A1* | 10/2006 | Partovi | G06F 19/322 |
| 2006/0239395 A1* | 10/2006 | Abe et al. | 378/1 |
| 2007/0106633 A1* | 5/2007 | Reiner | 707/1 |
| 2007/0118540 A1* | 5/2007 | Guo | 707/100 |
| 2007/0269117 A1* | 11/2007 | Ernvik | G06T 19/00 382/232 |
| 2008/0021740 A1* | 1/2008 | Beane | G06F 19/321 705/3 |
| 2008/0117230 A1* | 5/2008 | Wegenkittl et al. | 345/619 |
| 2008/0124002 A1* | 5/2008 | Eichhorn | 382/305 |
| 2008/0189317 A1* | 8/2008 | Wallace | G06F 19/321 |
| 2009/0103789 A1* | 4/2009 | Danner et al. | 382/128 |
| 2010/0036879 A1* | 2/2010 | Friese et al. | 707/104.1 |
| 2011/0150420 A1* | 6/2011 | Cordonnier | G06F 19/321 386/241 |
| 2011/0170755 A1* | 7/2011 | Buelow et al. | 382/128 |

* cited by examiner

| MODALITY=CR, CT, MR, US |

FIG.4B

| PORTION=HEAD |

FIG.4C

| FILE NUMBER=TOP |

FIG.5

| PATIENT NAME | TARO TOSHIBA |
|---|---|
| EXAMINATION DATE | JAN. 10, 2009 |
| FILE NUMBER | MODALITY |
| No. 001 | US |
| No. 002 | US |
| ⋮ | ⋮ |
| No. 101 | MR |
| No. 102 | MR |
| ⋮ | ⋮ |

FIG.11 ved and stored data onto a portable medium while carrying out diagnosis for a patient, the doctor cannot start to view the data instantly.

IMAGE DISPLAY METHOD, MEDICAL DIAGNOSTIC IMAGING APPARATUS, AND MEDICAL IMAGE PROCESSING APPARATUS

CROSS-REFERENCE TO RELATED APPLICATIONS

This application is based upon and claims the benefit of priority from the prior Japanese Patent Application No. 2009-11301, filed on Jan. 21, 2009; the entire contents of which are incorporated herein by reference.

BACKGROUND OF THE INVENTION

1. Field of the Invention

The present invention relates to an image display method, a medical diagnostic imaging apparatus, and a medical image processing apparatus.

2. Description of the Related Art

Recently, in order to use medical image data of a patient by a different hospital, medical image data collected by a medical diagnostic imaging apparatus is sometimes recorded on a portable medium, such as a Compact Disc (CD), or a Digital Versatile Disk (DVD), in some cases. Moreover, as well as medical image data, image display application for displaying the medical image data is often recorded on the portable medium. Accordingly, a doctor of a different hospital who receives the portable medium can view the medical image data only with a general purpose terminal device that has a function of reading data from a portable medium. In other words, the general purpose terminal device reads the image display application from a portable medium, starts the application, reads the medical image data stored in the portable medium, and displays the read data.

A portable medium is generally a medium with slow access, so that it takes some time to read data from it. For this reason, conventionally there has been a technology according to which data recorded on a CD is replicated into a magnetic disk in a terminal device in advance, and then the terminal device reads the data recorded on the magnetic disk (for example, JP-A H7-105067 (KOKAI)).

However, according to the conventional technology, there is a problem that it takes a long time until medical image data is displayed, as explained below.

When reading medical image data, the same medical image data is often repeatedly displayed, for example, a plurality of medical image data is viewed, or medical image data of a present examination and a past examination are viewed. When medical image data read from a portable medium into a terminal device is still present on a memory of the terminal device, fast access is available, and a time for repeatedly displaying the same medical image data is short. However, when displaying again medical image data that is once cleared from the memory, the medical image data needs to be read again from the portable medium with slow access, so that it needs some time.

For this reason, although it is conceivable to replicate medical image data recorded on a portable medium into a magnetic disk in a terminal device; in such case, replication itself also takes some time, thereby resulting in a long time until the medical image data is displayed. For example, when a doctor of a different hospital intends to view medical image data recorded on a portable medium while carrying out diagnosis for a patient, the doctor cannot start to view the data instantly.

SUMMARY OF THE INVENTION

According to one aspect of the present invention, an image display method includes reading setting information in which a sequence with medical meaning is set as a sequence of viewing a plurality of pieces of medical image data, from a portable medium that stores a plurality of pieces of medical image data and the setting information; replicating the pieces of medical image data stored in the portable medium into a storage unit of a terminal device to be used for viewing the medical image data as replicated medical image data in accordance with the sequence set in read setting information; starting to accept an output instruction that directs output of medical image data onto an output unit before replication of all of the pieces of medical image data stored in the portable medium is finished; searching the storage unit for replicated medical image data corresponding to medical image data specified in an output instruction to output medical image data, upon receiving the output instruction; and outputting searched-out replicated medical image data onto the output unit.

According to another aspect of the present invention, a medical diagnostic imaging apparatus includes a medical image-data taking unit that takes medical image data; a medical image-data writing unit that writes a plurality pieces of medical image data taken by the medical image-data taking unit onto a portable medium; a setting-information writing unit that writes setting information in which a sequence with medical meaning is set as a sequence of viewing the pieces of medical image data onto the portable medium; and a program writing unit that writes onto the portable medium a computer program that causes a computer to execute reading the setting information from the portable medium, replicating the pieces of medical image data stored in the portable medium into a storage unit of a terminal device to be used for viewing the medical image data as replicated medical image data in accordance with a sequence set in the setting information, starting to accept an output instruction that directs output of medical image data onto an output unit before replication of all medical image data stored in the portable medium is finished, searching the storage unit for replicated medical image data corresponding to medical image data specified in an output instruction upon receiving the output instruction, and outputting searched-out replicated medical image data onto the output unit.

According to still another aspect of the present invention, a medical image processing apparatus includes a medical image-data writing unit that writes a plurality pieces of medical image data onto a portable medium; a setting-information writing unit that writes setting information in which a sequence with medical meaning is set as a sequence of viewing the pieces of medical image data onto the portable medium; and a program writing unit that writes onto the portable medium a computer program that causes a computer to execute reading the setting information from the portable medium, replicating the pieces of medical image data stored in the portable medium into a storage unit of a terminal device to be used for viewing the medical image data as replicated medical image data in accordance with a sequence set in the setting information, starting to accept an output instruction that directs output of medical image data onto an output unit before replication of all medical image data stored in the portable medium is finished, searching the storage unit for replicated medical image data corresponding to medical image data specified in an output instruction upon receiving the output instruction, and outputting searched-out replicated medical image data onto the output unit.

DETAILED DESCRIPTION OF THE INVENTION

Exemplary embodiments of the present invention will be explained below in detail with reference to the accompanying drawings. A medical diagnostic imaging apparatus and a medical image processing apparatus are each an apparatus that writes medical image data and an image display program (also referred to as image display application) onto a portable medium. At first, a first embodiment of the present invention is explained below about a medical image display apparatus that is a general purpose terminal device that executes image display application; then a second embodiment of the present invention is explained below about a medical diagnostic imaging apparatus; and a third embodiment of the present invention is explained below about a medical image processing apparatus.

Figure 1:
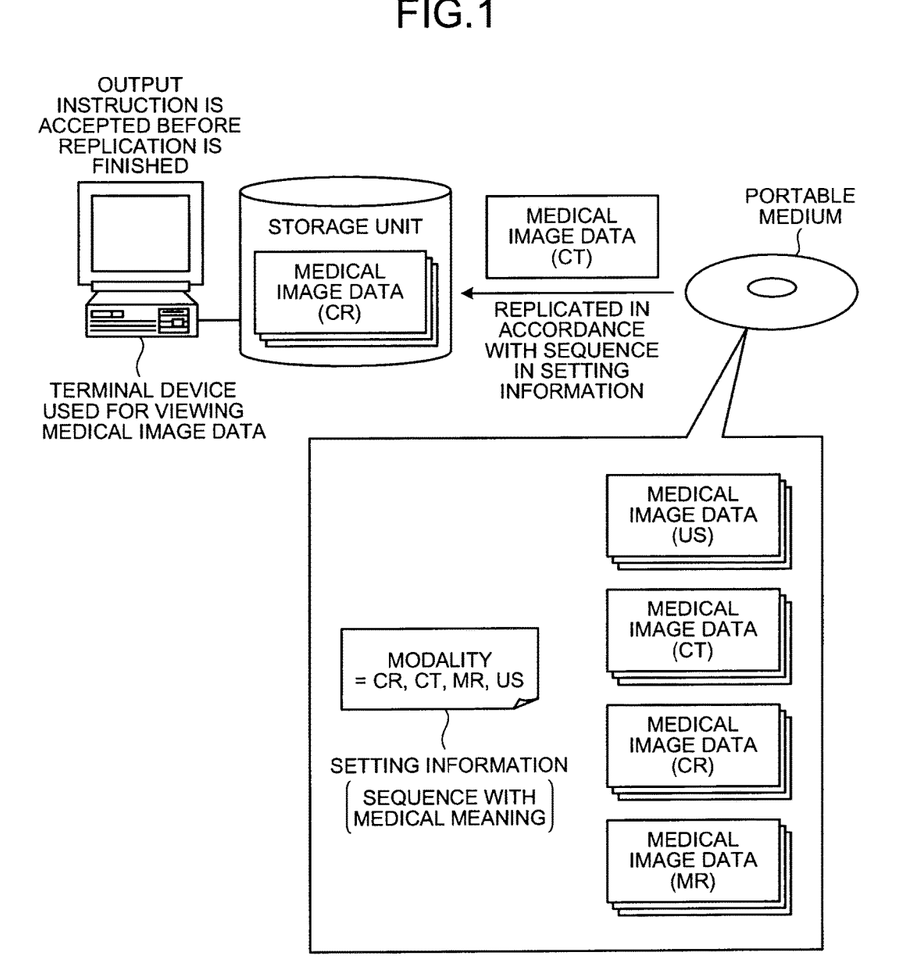
FIG. 1 is a schematic diagram for explaining an outline of image display application according to a first embodiment of the present invention.

First of all, an outline of image display application according to the first embodiment is explained below with reference to FIG. 1. FIG. 1 is a schematic diagram for explaining an outline of the image display application.

As shown in FIG. 1, setting information and a plurality of medical image data are recorded on a portable medium. The setting information is that a sequence with medical meaning is set as the sequence of viewing a plurality of medical image data. Medical image data are sometimes collected by a plurality of medical diagnostic imaging apparatuses in some cases. Consequently, for example, as shown in FIG. 1, the portable medium includes medical image data recorded thereon that are collected by an ultrasound diagnosis apparatus, an X-ray Computed Tomography (CT) apparatus, a Computed Radiography (CR) apparatus, and a Magnetic Resonance Imaging (MRI) apparatus.

It is assumed that, for example, as shown in FIG. 1, "modality=CR, CT, MR, US" is set in setting information. This means that viewing of medical image data collected by the CR apparatus, medical image data collected by the X-ray CT apparatus, medical image data collected by the MRI apparatus, and medical image data collected by the ultrasound diagnosis apparatus in this order is given with medical meaning, as the sequence of viewing medical image data recorded on the same portable medium as a portable medium on which the setting information is recorded.

Such setting information is that, for example, when writing medical image data of a patient onto a portable medium, an engineer or a doctor sets a sequence with medical meaning as the sequence of viewing medical image data.

When a terminal device used for viewing medical image data receives input of a portable medium, image display application reads setting information from the portable medium, and then replicates a plurality medical image data recorded on the portable medium into a storage unit of the terminal device as replicated medical image data in accordance with a sequence set in the read setting information. Hereinafter, when distinguishing medical image data stored in a portable medium from medical image data stored in a storage unit of a terminal device, the latter is referred to as "replicated medical image data".

For example, the image display application reads setting information set as "modality=CR, CT, MR, and US", and replicates medical image data collected by the CR apparatus, medical image data collected by the X-ray CT apparatus, medical image data collected by the MRI apparatus, and medical image data collected by the ultrasound diagnosis apparatus in this order.

Moreover, the image display application starts to accept an output instruction that directs output of medical image data to an output unit before replication of all medical image data recorded on the portable medium is finished.

Upon receiving an output instruction to output medical image data, the image display application searches the storage unit with respect to medical image data specified in the output instruction, reads from the storage unit replicated medical image data corresponding to the medical image data specified in the output instruction, and outputs the read data to the output unit.

For example, when receiving an output instruction to output medical image data collected by the CR apparatus, the storage unit is searched with respect to the medical image data collected by the CR apparatus, and corresponding replicated medical image data is read from the storage unit, and output to the output unit.

If replication of the medical image data collected by the CR apparatus is finished when receiving the output instruction, corresponding replicated medical image data can be searched out from the storage unit. Because the sequence set in the setting information is a sequence with medical meaning as the sequence of viewing a plurality of medical image data, it is conceivable that the output instruction is highly likely carried out in a sequence similar to that in the setting information. Therefore, it is highly probable that replication of medical image data specified in the output instruction is finished.

In this way, according to the image display application according to the first embodiment, replication of medical image data is performed through background processing in accordance with a sequence with medical meaning as the sequence of viewing a plurality of medical image data, and reception of an output instruction is started before replication of all medical image data recorded on a portable medium is finished, so that a time until medical image data is displayed can be reduced.

Figure 2:
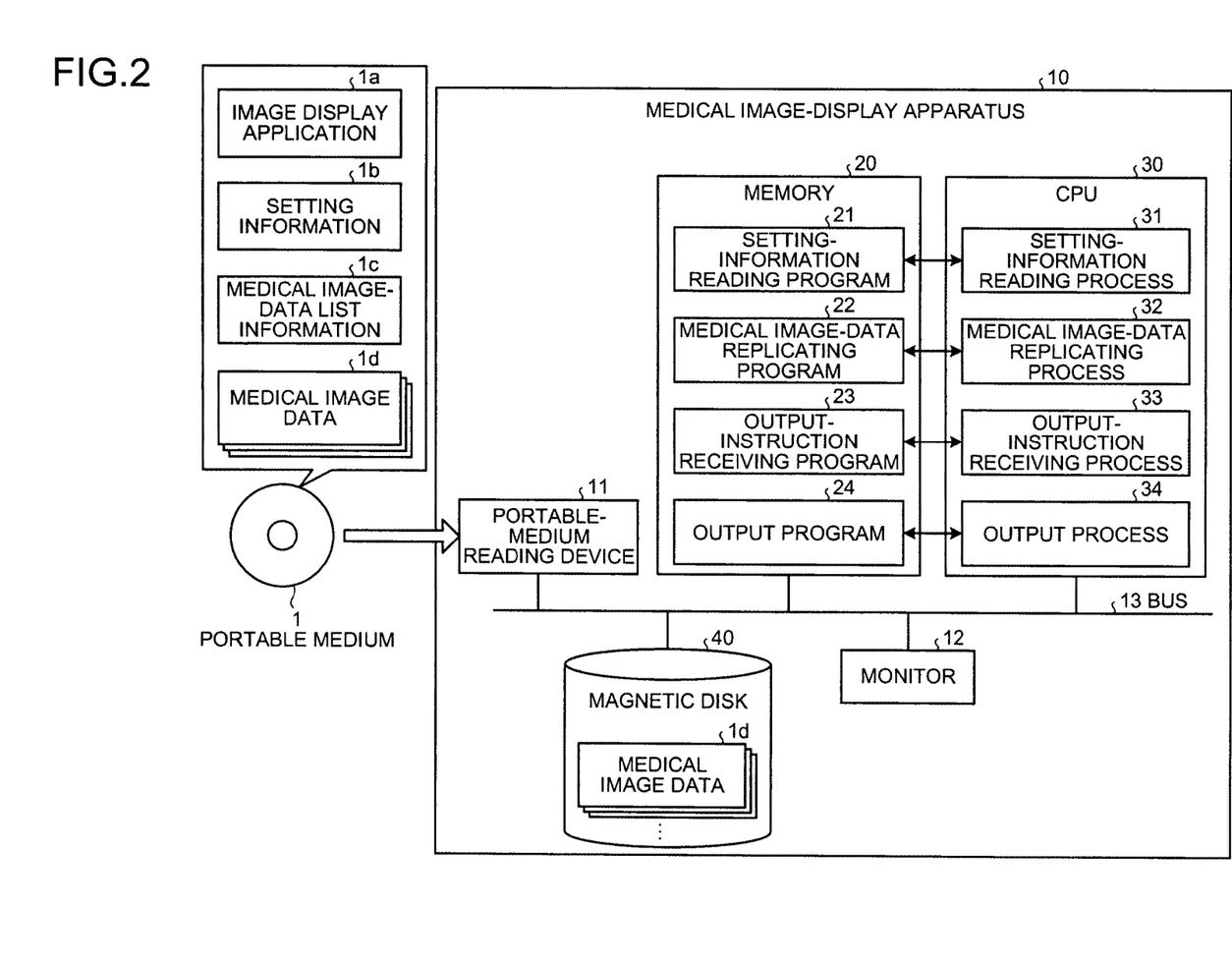
FIG. 2 is a functional block diagram of a configuration of a medical image display apparatus configured to execute the image display application.
Figure 3:
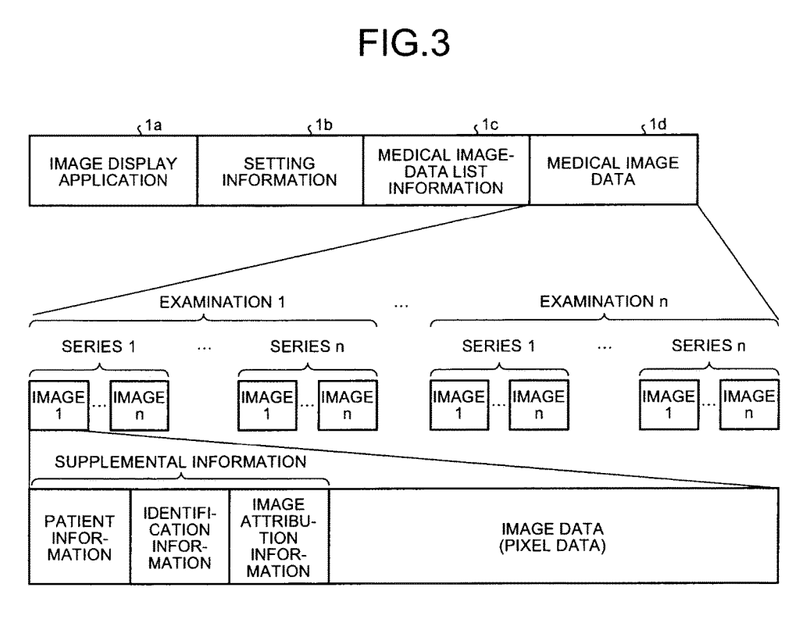
FIG. 3 is a schematic diagram for explaining a data structure of data recorded on a portable medium.
Figure 4A:
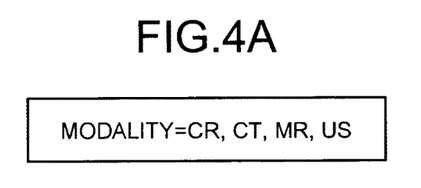
FIGS. 4A to 4C are schematic diagrams for explaining setting information.
Figure 4B:
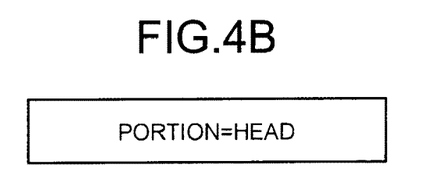
Figure 4C:
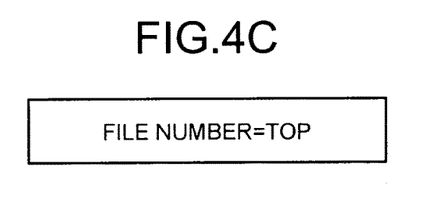
Figure 5:
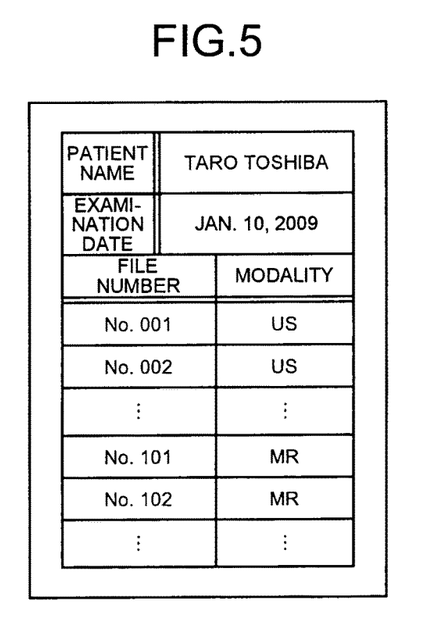
FIG. 5 is a schematic diagram for explaining medical image data list information.
Figure 6A:
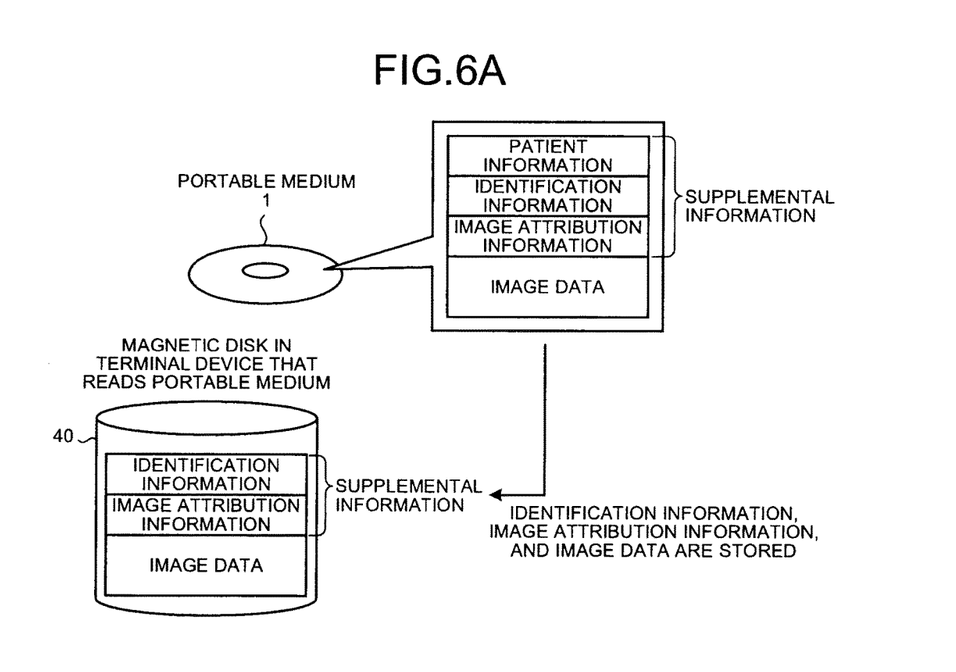
FIGS. 6A and 6B are schematic diagrams for explaining replication of supplemental information.
Figure 6B:
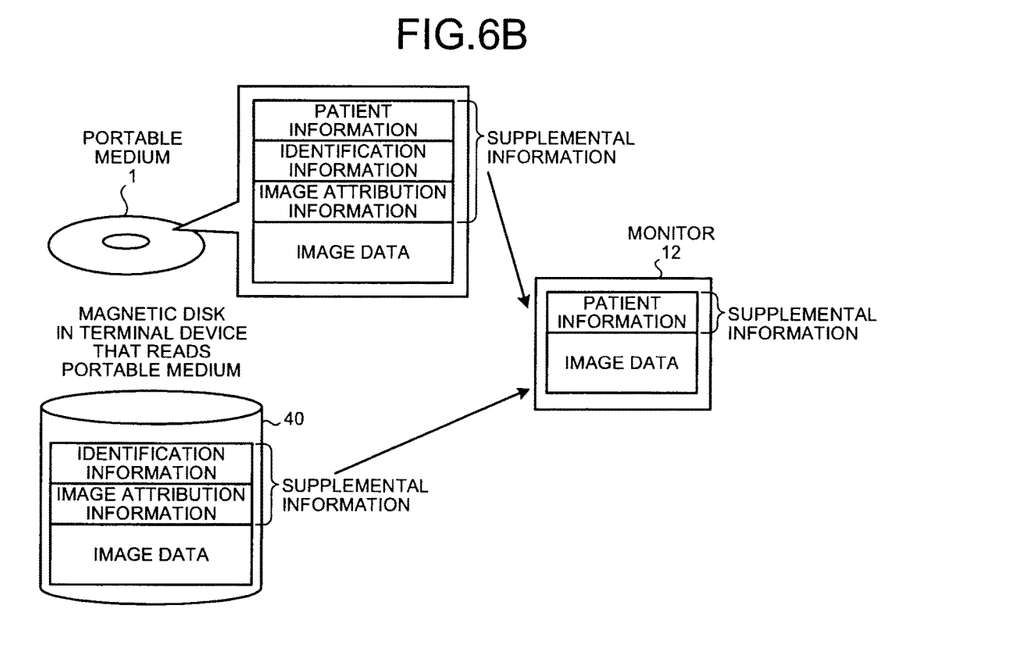
Figure 7:
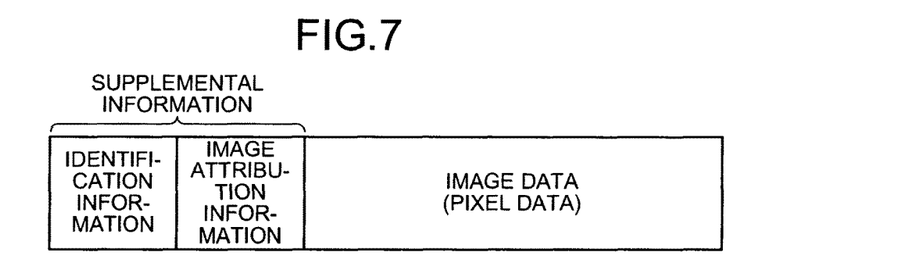
FIG. 7 is a schematic diagram for explaining a data structure of data stored in a magnetic disk.

Then, a configuration of the medical image display apparatus configured to execute the image display application is explained below with reference to FIGS. 2 to 7. FIG. 2 is a functional block diagram of a configuration of the medical image display apparatus configured to execute the image display application. FIG. 3 is a schematic diagram for explaining a data structure of data recorded on a portable medium. FIGS. 4A to 4C are schematic diagrams for explaining setting information. FIG. 5 is a schematic diagram for explaining medical image data list information. FIGS. 6A and 6B are schematic diagrams for explaining replication of supplemental information. FIG. 7 is a schematic diagram for explaining a data structure of data stored in a magnetic disk.

As shown in FIG. 2, image display application 1a, setting information 1b, medical image-data list information 1c, and medical image data 1d are recorded on a portable medium 1 according to the first embodiment, which has a data structure, for example, as shown in FIG. 3.

The image display application 1a is application software configured to be stored in a memory 20 of a medical image-display apparatus 10 and to operate on the medical image-display apparatus 10, and is for displaying the medical image data 1d similarly recorded on the portable medium 1 onto a monitor 12 of the medical image-display apparatus 10.

The setting information 1b is information describing setting information that defines operation of the image display application 1a, and includes a sequence with medical meaning set as the sequence of viewing the medical image data 1d that is also recorded on the portable medium 1.

The setting information 1b is, for example, data as shown in FIGS. 4A to 4C. The setting information 1b shown in FIG. 4A as an example is given with medical meaning to viewing of medical image data collected by a CR apparatus, medical image data collected by an X-ray CT apparatus, medical image data collected by an MRI apparatus, and medical image data collected by an ultrasound diagnosis apparatus in this order. Moreover, the setting information 1b shown in FIG. 4B as an example is given with medical meaning to viewing of data from medical image data of a head that is imaged (for example, the head is a primary focus). In addition, other cases, for example, where viewing of data from a foot, or a center portion is given with medical meaning, are also conceivable. Furthermore, the setting information 1b shown in FIG. 4C as an example is given with medical meaning to viewing of data sequentially from the beginning of the file numbers. Sequences with medical meaning are not limited to the examples in FIGS. 4A to 4C.

The medical image-data list information 1c is, for example, file information about the medical image data 1d recorded on the portable medium 1. For example, as shown in FIG. 5, the medical image-data list information 1c is information that associates, such as a patient name and an examination date, a file number, and modality with each other.

The medical image data 1d is data that is collected by imaging a subject by the medical diagnostic imaging apparatus. Specifically, medical image data according to the first embodiment is groups of a plurality of images, and the groups of images are recorded by being grouped into examination units. It is assumed that a plurality of series is present in one examination, and a plurality of images is present in one series. Therefore, for example, as shown in FIG. 3, the medical image data 1d has a data structure such that data is recorded unit by unit of examination, a plurality of series is recorded in one examination, and a plurality of images is recorded in one series.

Moreover, as shown in FIG. 3, one image includes supplemental information and image data (pixel data that is data itself of the image). The supplemental information is patient information, identification information, and image attribution information. The patient information is attribution information about a subject who is imaged into medical image data, and including private information, such as a patient name and a date of birth. On the other hand, the identification information is information that uniquely identifies medical image data, which is, for example, Service Object Pair (SOP) instance Unique Identifier (UID) of Digital Imaging and Communications in Medicine (DICOM). The image attribution information is attribution information about image data, which is, for example, conditions for displaying image data onto the monitor 12 (for example, the size, the color, and the imaging conditions of an image). According to the first embodiment, it is assumed that each of the file numbers described above is given to unit by unit, that is "image 1", or "image n", present in one series.

Returning to FIG. 2, the medical image-display apparatus 10 is a general purpose terminal device that executes the image display application 1a, and is connected to a portable-medium reading device 11, the monitor 12, the memory 20, a Central Processing Unit (CPU) 30, and a magnetic disk 40, via a bus 13, as shown in FIG. 2.

When the portable medium 1 is input into the portable-medium reading device 11, the medical image-display apparatus 10 reads the image display application 1a recorded on the portable medium 1 into the memory 20, and stores it as a setting-information reading program 21, a medical image-data replicating program 22, an output-instruction receiving program 23, and an output program 24, as shown in FIG. 2. These programs turn to a setting-information reading process 31, a medical image-data replicating process 32, an output-instruction receiving process 33, and an output process 34, on the CPU 30, and operate on the medical image-display apparatus 10. As a result of that the programs operate on the medical image-display apparatus 10, the medical image data 1d recorded on the portable medium 1 is replicated and stored into the magnetic disk 40, and the medical image data 1d (replicated medical image data) stored in the magnetic disk 40 is output onto the monitor 12.

The setting-information reading program 21 reads the setting information 1b from the portable medium 1.

The medical image-data replicating program 22 replicates a plurality of the medical image data 1d recorded on the portable medium 1 into the magnetic disk 40 in accordance with a sequence set in the setting information 1b read by the setting-information reading program 21.

For example, when the setting information 1b is the setting information 1b shown in FIG. 4A as an example, the medical image-data replicating program 22 refers to the medical image-data list information 1c recorded on, such as the portable medium 1, and extracts file numbers such that modalities are sequenced in order of "CR", "CT", "MR", and "US". If an applicable modality is not present, the file numbers can be extracted in a sequence in which the modality is excluded. The medical image-data replicating program 22 then replicates the medical image data 1d recorded on the portable medium 1 into the magnetic disk 40 in accordance with the sequence of the extracted file numbers.

When replicating, as shown in FIG. 6A, the medical image-data replicating program 22 according to the first embodiment replicates data except patient information among the medical image data 1d into the magnetic disk 40. Precisely, the medical image-data replicating program 22 replicates identification information, image attribution information, and image data into the magnetic disk 40, so that a data structure stored in the magnetic disk 40 is as shown in FIG. 7.

When the setting information 1b is the setting information 1b shown in FIG. 4B as an example, the medical image-data replicating program 22 acquires portion information by referring to, for example, supplemental information included in the medical image data 1d piece by piece, and replicates into the magnetic disk 40 pieces of data in order from the medical image data 1d from which portion information "head" is acquired. Moreover, when the setting information 1b is the setting information 1b shown in FIG. 4C as an example, the medical image-data replicating program 22 refers to, for example, the medical image-data list information 1c recorded on the portable medium 1, acquires that the beginning of the file numbers is "001", and replicates data into the magnetic disk 40 from the file number "001".

The output-instruction receiving program 23 starts to accept an output instruction that directs output of medical image data onto the monitor 12 before replication of all of the medical image data 1d recorded on the portable medium 1 is finished by the medical image-data replicating program 22. In other words, the replication by the medical image-data replicating program 22 is performed through background processing.

For example, the output-instruction receiving program 23 accepts an output instruction by outputting the medical image-data list information 1c recorded on the portable medium 1, and then receiving selection of a file number.

When an output instruction is received by the output-instruction receiving program 23, the output program 24 searches preferentially the magnetic disk 40 with respect to a specific piece of the medical image data 1d specified in the output instruction, reads a corresponding piece of the medical image data 1d (replicated medical image data) from the magnetic disk 40, and outputs the read data onto the monitor 12. For example, the output program 24 searches the magnetic disk 40 by using a file number of which selection is received.

When searching, as shown in FIG. 6B, the output program 24 according to the first embodiment searches the portable medium 1 by using identification information included in the searched-out piece of the medical image data 1d (replicated medical image data), and outputs patient information that is stored by being associated with the identification information together with the medical image data 1d (replicated medical image data) searched out from the magnetic disk 40 onto the monitor 12. Alternatively, the output program 24 can search the portable medium 1 by using a file number instead of identification information as supplemental information, and can output patient information recorded as data of the file number together with the medical image data 1d (replicated medical image data) searched out from the magnetic disk 40, onto the monitor 12. Moreover, the output program 24 according to the first embodiment outputs the medical image data 1d (replicated medical image data) in accordance with image attribution information included in the searched-out piece of the medical image data 1d (replicated medical image data), onto the monitor 12. In other words, image attribution information is conditions for displaying a replicated piece of the medical image data 1d onto the monitor 12, and the output program 24 outputs the medical image data 1d (replicated medical image data) onto the monitor 12 in accordance with conditions specified by the image attribution information. The monitor 12 can display thereon identification information and image attribution information. In such case, those information can be read from any of the portable disk and the magnetic disk.

Figure 8:
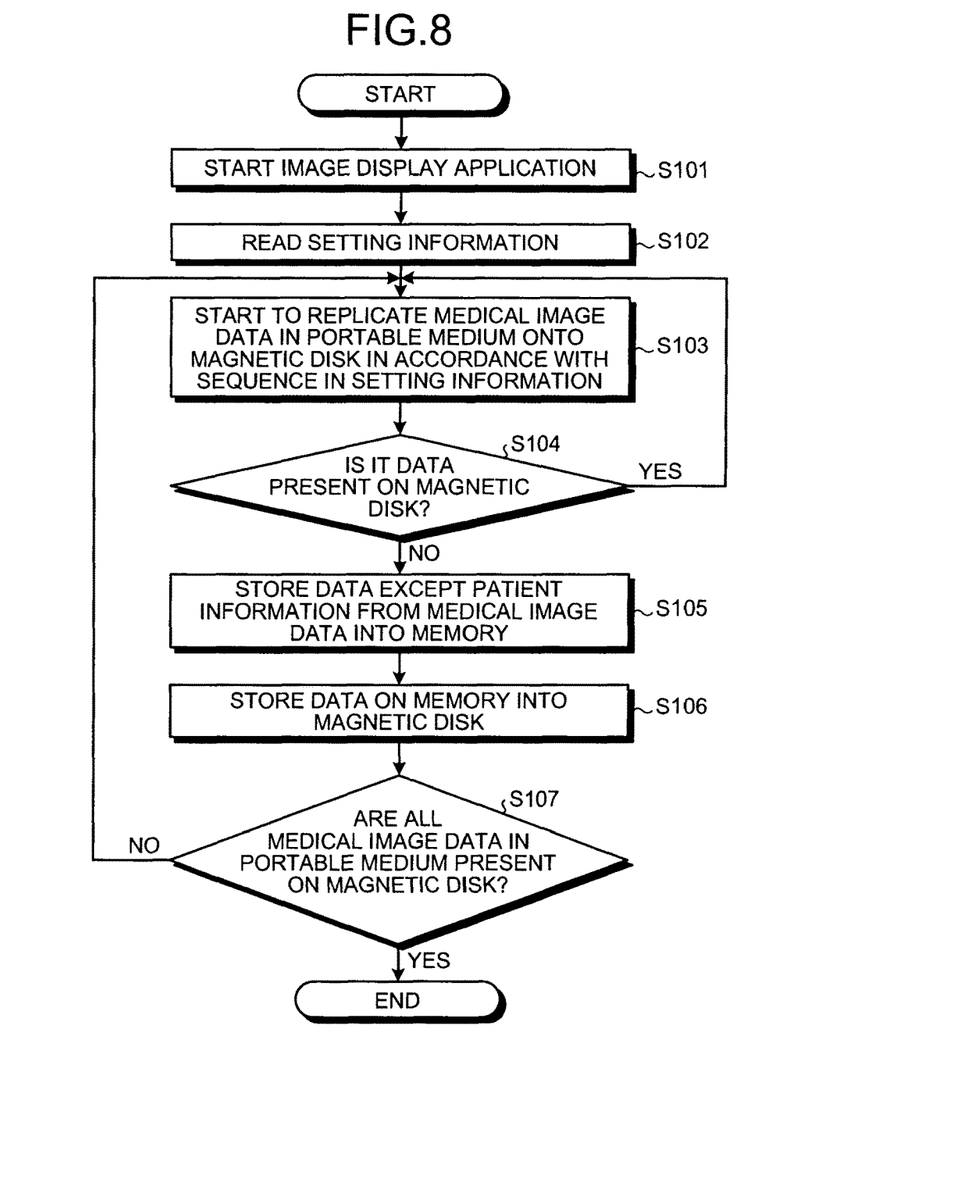
FIG. 8 is a flowchart of a replication process procedure for medical image data according to the first embodiment.
Figure 9:
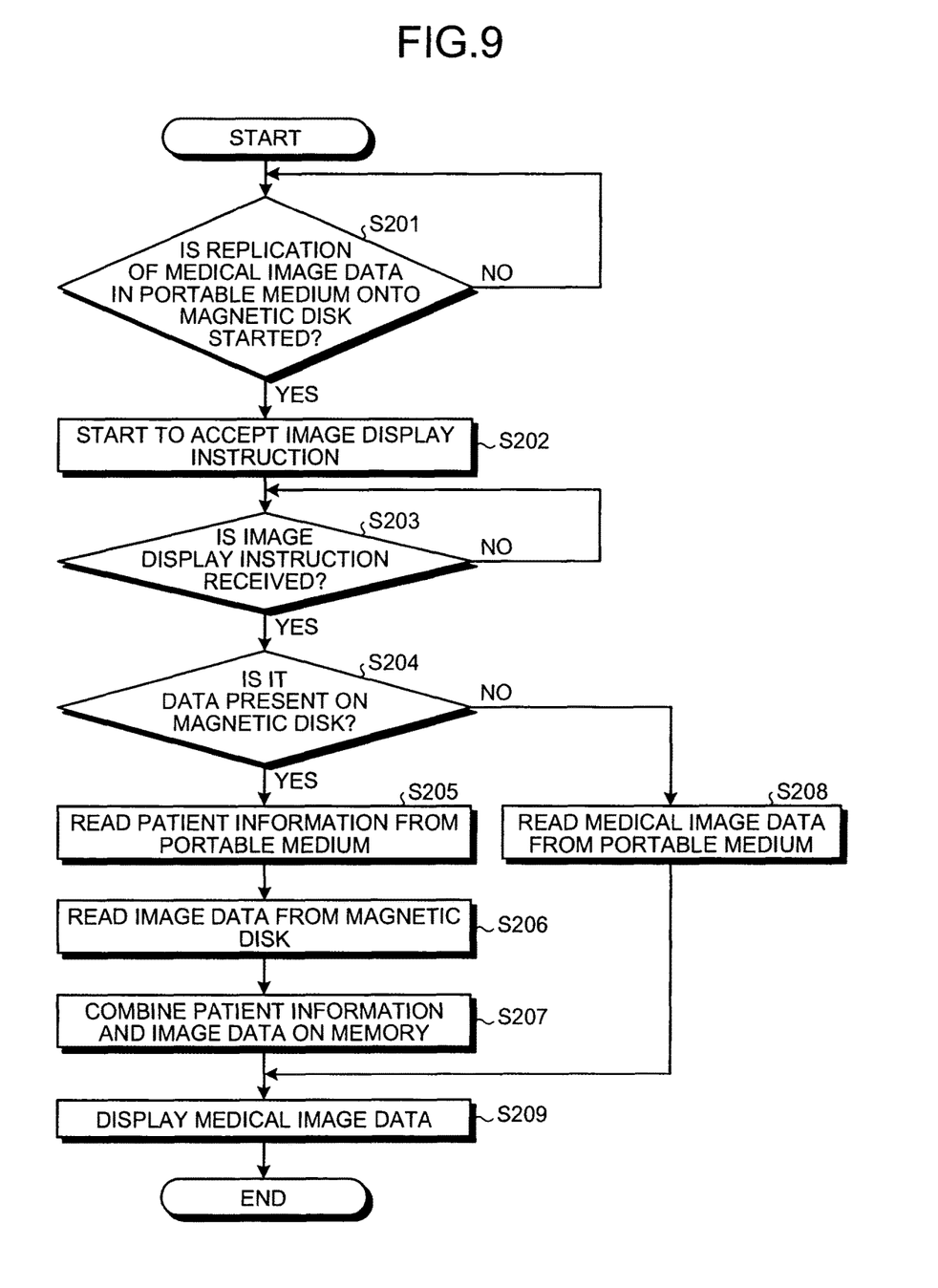
FIG. 9 is a flowchart of an output process procedure for medical image data according to the first embodiment.

A process procedure according to the image display application is explained below with reference to FIGS. 8 and 9. FIG. 8 is a flowchart of a replication process procedure for medical image data. FIG. 9 is a flowchart of an output process procedure for medical image data.

First of all, as shown in FIG. 8, when the portable medium 1 is inserted into the portable-medium reading device 11, the medical image-display apparatus 10 reads the image display application 1a recorded on the portable medium 1 into the memory 20, and starts the image display application 1a with timing of reading (or timing specified by a user) (Step S101).

Then, the setting-information reading program 21 reads the setting information 1b from the portable medium 1 (Step S102).

The medical image-data replicating program 22 then starts to replicate a plurality of the medical image data 1d into the magnetic disk 40 in accordance with a sequence set in the setting information 1b read by the setting-information reading program 21 (Step S103). For example, when the setting information 1b is the setting information 1b shown in FIG. 4A as an example, the medical image-data replicating program 22 refers to the medical image-data list information 1c recorded on, such as the portable medium 1, extracts file numbers such that modalities are sequenced in order of "CR", "CT", "MR", and "US", and replicates the medical image data 1d recorded on the portable medium 1 into the magnetic disk 40 in accordance with the sequence of the extracted file numbers.

The medical image-data replicating program 22 selects one file to be a candidate of replication, and determines whether it is a file already stored in the magnetic disk 40 (Step S104). If the selected file is a file already stored in the magnetic disk 40 (Yes at Step S104), the medical image-data replicating program 22 goes back to the processing at Step S103, and transits to replication of a next candidate.

By contrast, if the selected file is not file stored in the magnetic disk 40 (No at Step S104), the medical image-data replicating program 22 stores data except patient information among the medical image data 1d into the memory 20 (Step S105), and stores the data stored in the memory 20 into the magnetic disk 40 (Step S106).

The medical image-data replicating program 22 then determines whether all of the medical image data 1d recorded on the portable medium 1 are present on the magnetic disk 40 (Step S107); and if all replication is completed (Yes at Step S107), the processing is terminated. By contrast, if replication is not fully completed (No at Step S107), the medical image-data replicating program 22 goes back to the processing at Step S103, and transits to replication of a next candidate.

As shown in FIG. 9, the output-instruction receiving program 23 determines whether replication by the medical image-data replicating program 22 is started (Step S201). If it is determined that the replication is not started (No at Step S201), the output-instruction receiving program 23 goes back to the processing of determining whether replication by the medical image-data replicating program 22 is started.

By contrast, if it is determined that the replication is started (Yes at Step S201), the output-instruction receiving program 23 starts to accept an image display instruction (Step S202). For example, the output-instruction receiving program 23 outputs the medical image-data list information 1c recorded on the portable medium 1 onto the monitor 12, and starts to accept selection of a file number.

The output program 24 then determines whether an image display instruction is received by the output-instruction receiving program 23 (Step S203); and if it is determined that the image display instruction is received (Yes at Step S203), the output program 24 searches the magnetic disk 40 by using the file number of which selection is received (Step S204).

As a result of searching the magnetic disk 40, if the search is successful (Yes at Step S204), the output program 24 searches the portable medium 1 by using identification information included in the searched-out piece of the medical image data 1d (replicated medical image data), and reads patient information that is stored by being associated with the identification information into the memory 20 (Step S205).

Subsequently, the output program 24 reads image data of a search result from the magnetic disk 40 into the memory 20 (Step S206), and combines the patient information read into the memory 20 at Step S205, and the image data read into the memory 20 at Step S206, on the memory 20 (Step S207).

By contrast, if the search is not successful as a result of searching the magnetic disk 40 at Step S204 (No at Step S204), the output program 24 reads a corresponding piece of the medical image data 1d from the portable medium 1 (Step S208).

After that, the output program 24 displays the medical image data 1d onto the monitor 12 (Step S209). For example, if the medical image data 1d (replicated medical image data) is successfully searched out at Step S204, the output program 24 outputs the patient information and the image data combined on the memory 20 onto the monitor 12 in accordance with image attribution information included in the medical image data 1d (replicated medical image data). By contrast, if the medical image data 1d (replicated medical image data) is not successfully searched out at Step S204, the output program 24 outputs patient information and image data read from the portable medium 1 onto the monitor 12 in accordance with image attribution information included in the medical image data 1d read from the portable medium 1.

As described above, the image display application 1a according to the first embodiment reads the setting information 1b in which a sequence with medical meaning is set as the sequence of viewing a plurality of medical image data, from the portable medium 1 that stores therein a plurality of the medical image data 1d and the setting information 1b. The image display application 1a then replicates a plurality of the medical image data 1d stored in the portable medium 1 into the magnetic disk 40 in the medical image-display apparatus 10 used for viewing the medical image data 1d, in accordance with the sequence set in the setting information 1b that is read. Moreover, the image display application 1a starts to accept an output instruction that directs output of the medical image data 1d onto the monitor 12 before replication is finished with respect to all of the medical image data 1d stored in the portable medium 1. Upon receiving an output instruction to output the medical image data 1d, the image display application 1a then searches the magnetic disk 40 with respect to a specific piece of the medical image data 1d specified in the output instruction, and reads a corresponding piece of the medical image data 1d (replicated medical image data) from the magnetic disk 40, and outputs the read data onto the monitor 12.

In this way, according to the image display application 1a according to the first embodiment, replication of medical image data is performed through background processing in accordance with a sequence with medical meaning as the sequence of viewing a plurality of medical image data, and reception of an output instruction is started before replication of all medical image data recorded on a portable medium is finished, so that a time until medical image data is displayed can be reduced.

Moreover, the medical image data 1d includes patient information about a subject imaged into the medical image data 1d as supplemental information, and the image display application 1a replicates data except the patient information among the medical image data 1d into the magnetic disk 40. In this way, the image display application 1a according to the first embodiment can ensure security without carelessly replicating patient information.

Furthermore, the medical image data 1d includes patient information about a subject imaged into the medical image data 1d and identification information that uniquely identifies the medical image data 1d as supplemental information, and the image display application 1a replicates data except the patient information among the medical image data 1d into the magnetic disk 40. The image display application 1a then searches the magnetic disk 40 with respect to a specific piece of the medical image data 1d specified in an output instruction, and searches the portable medium 1 by using identification information included in the medical image data 1d (replicated medical image data) read from the magnetic disk 40. Subsequently, the image display application 1a outputs patient information that is stored by being associated with identification information onto the monitor 12 together with the medical image data 1d (replicated medical image data) searched out from the magnetic disk 40.

In this way, the image display application 1a according to the first embodiment is capable not only to ensure security without carelessly replicating patient information, but also to display the patient information when displaying.

Moreover, the medical image data 1d includes image attribution information in addition to patient information about a subject imaged into the medical image data 1d and identification information that uniquely identifies the medical image data 1d as supplemental information, and the image display application 1a replicates data except the patient information among the medical image data 1d into the magnetic disk 40. The image display application 1a then searches the magnetic disk 40 with respect to a specific piece of the medical image data 1d specified in an output instruction, and outputs the medical image data 1d (replicated medical image data) read from the magnetic disk 40 onto the monitor 12 in accordance with the image attribution information included in the medical image data 1d (replicated medical image data).

In this way, the image display application 1a according to the first embodiment is capable not only to ensure security without carelessly replicating patient information, but also to display the patient information and to display a medical image appropriately in accordance with display conditions that are prepared in advance, when displaying.

Figure 10:
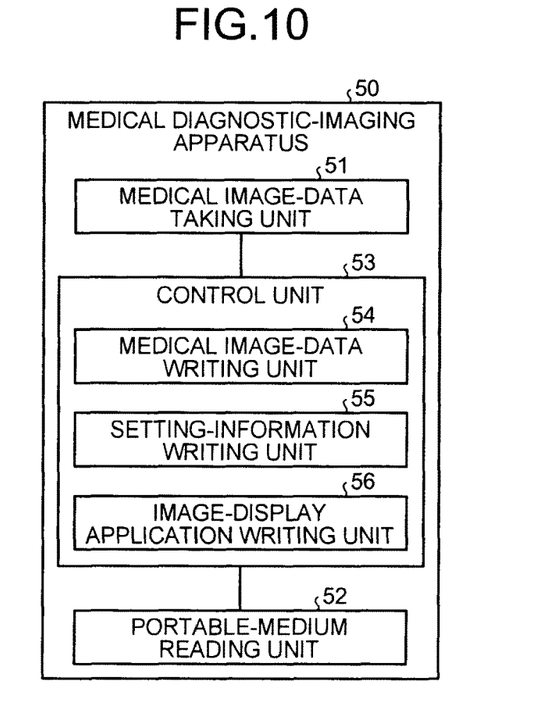
FIG. 10 is a functional block diagram of a configuration of a medical diagnostic imaging apparatus according to a second embodiment of the present invention.

A second embodiment of the present invention is explained below. Although the first embodiment is explained above about the image display application, the second embodiment is explained below about a medical diagnostic imaging apparatus that writes image display application onto a portable medium. FIG. 10 is a functional block diagram of a configuration of a medical diagnostic imaging apparatus.

The medical diagnostic imaging apparatus according to the second embodiment can be, for example, a Computed Radiography (CR) apparatus, an X-ray Computed Tomography (CT) apparatus, a Magnetic Resonance Imaging (MRI) apparatus, or an ultrasound diagnosis apparatus.

A medical diagnostic-imaging apparatus 50 includes, for example, as shown in FIG. 10, a medical image-data taking unit 51, a portable-medium reading unit 52, and a control unit 53. The control unit 53 includes a medical image-data writing unit 54, a setting-information writing unit 55, and an image-display application writing unit 56.

The medical image-data taking unit 51 takes medical image data. The portable-medium reading unit 52 reads a portable medium.

The medical image-data writing unit 54 writes medical image data onto a portable medium. Specifically, the medical image-data writing unit 54 medical image data taken by the medical image-data taking unit 51 onto a portable medium that is read by the portable-medium reading unit 52.

The setting-information writing unit 55 writes setting information in which a sequence with medical meaning is set as the sequence of viewing a plurality of medical image data, onto a portable medium. Specifically, the setting-information writing unit 55 writes setting information that is set by, for example, an engineer or a doctor, onto a portable medium read by the portable-medium reading unit 52.

The image-display application writing unit 56 writes image display application that has a function similar to the image display application 1a explained in the first embodiment, onto a portable medium. Specifically, the image-display application writing unit 56 writes, onto a portable medium read by the portable-medium reading unit 52, a computer program that causes a computer to execute: reading setting information from a portable medium; replicating a plurality of medical image data stored in the portable medium into a storage unit of a terminal device to be used for viewing the medical image data as replicated medical image data in accordance with a sequence set in the setting information; starting to accept an output instruction that directs output of medical image data onto an output unit before replication of all medical image data stored in the portable medium is finished; upon receiving an output instruction, searching the storage unit with respect to medical image data specified in the output instruction; reading corresponding replicated medical image data from the storage unit; and outputting the read data to the output unit.

In this way, the medical diagnostic imaging apparatus according to the second embodiment can create a portable medium on which image display application that achieves reduction in a time until medical image data is displayed, setting information, and medical image data are written.

Figure 11:
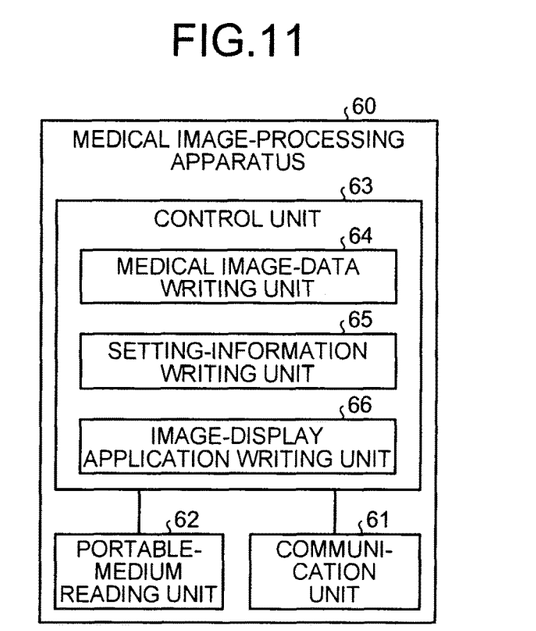
FIG. 11 is a functional block diagram of a configuration of a medical image processing apparatus according to a third embodiment of the present invention.

A third embodiment of the present invention is explained below. Although the second embodiment is explained above about the medical diagnostic imaging apparatus that writes image display application onto a portable medium, the third embodiment is explained below about a medical image processing apparatus that writes image display application onto a portable medium. FIG. 11 is a functional block diagram of a configuration of a medical image processing apparatus.

The medical image processing apparatus according to the third embodiment is a terminal device of an image display system (for example, Picture Archiving and Communication System (PACS)) that is connected via a network to a diagnosis apparatus, for example, a CR apparatus, an X-ray CT apparatus, an MRI apparatus, or an ultrasound diagnosis apparatus.

A medical image-processing apparatus 60 includes, for example, as shown in FIG. 11, a communication unit 61, a portable-medium reading unit 62, and a control unit 63. The control unit 63 includes a medical image-data writing unit 64, a setting-information writing unit 65, and an image-display application writing unit 66.

The communication unit 61 acquires medical image data from such as a diagnosis apparatus connected via a network. The portable-medium reading unit 62 reads a portable medium.

The medical image-data writing unit 64 writes medical image data onto a portable medium. Specifically, the medical image-data writing unit 64 writes medical image data acquired by the communication unit 61 onto a portable medium that is read by the portable-medium reading unit 62.

The setting-information writing unit 65 writes setting information in which a sequence with medical meaning is set as the sequence of viewing a plurality of medical image data, onto a portable medium. Specifically, the setting-information writing unit 65 writes setting information that is set by, for example, an engineer or a doctor, onto a portable medium that is read by the portable-medium reading unit 62.

The image-display application writing unit 66 writes image display application that has a function similar to the image display application 1a explained in the first embodiment, onto a portable medium. Specifically, the image-display application writing unit 66 writes, onto a portable medium read by the portable-medium reading unit 62, a computer program that causes a computer to execute: reading setting information from a portable medium; replicating a plurality of medical image data stored in the portable medium into a storage unit of a terminal device to be used for viewing the medical image data as replicated medical image data in accordance with a sequence set in the setting information; starting to accept an output instruction that directs output of medical image data onto an output unit before replication of all medical image data stored in the portable medium is finished; upon receiving an output instruction, searching the storage unit with respect to medical image data specified in the output instruction; reading corresponding replicated medical image data from the storage unit; and outputting the read data to the output unit.

In this way, the medical image processing apparatus according to the third embodiment can create a portable medium on which image display application that achieves reduction in a time until medical image data is displayed, setting information, and medical image data are written.

The first to third embodiments of the present invention have been explained above, and in addition to the above embodiments, the present invention can be implemented in various different forms.

Although the first embodiment is explained above in a case where image display application is stored in a portable medium together with medical image data and setting information, the present invention is not limited to this. Image-display application can be preliminarily installed in a terminal device to be used for viewing medical image data, for example. When setting information is stored in a terminal device, the present invention can also be similarly applied. It is effective when it is desired to set a sequence of viewing medical image data stored in a portable medium ex post facto.

Moreover, although the first embodiment is explained above about the method of replicating data except patient information when the image display application replicates medical image data, the present invention is not limited to this. If replication of patient information has no particular problem, patient information can be replicated together with image data.

Furthermore, although the first embodiment is explained above about the example that the image display application starts reception of an output instruction simultaneously when replication of medical image data is started, the present invention is not limited to this, so that reception of an output instruction can be started, for example, after a certain time has elapsed.

Moreover, although the first embodiment is explained above about the method by which the output-instruction receiving program 23 outputs the medical image-data list information 1c to the monitor 12 and receives selection of the numbers of files, the present invention is not limited to this. For example, it can be a method by which a first piece of the medical image data 1d (replicated medical image data) is output onto the monitor 12 in accordance with a sequence set in the setting information without outputting the medical image-data list information 1c onto the monitor 12, and then, for example, by receiving a press of a "to next" button, a next piece of the medical image data 1d (replicated medical image data) indicated by the sequence set in the setting information is output onto the monitor 12. In other words, when the output-instruction receiving program 23 receives, for example, a press of the "to next" button, the output program 24 searches for a piece of the medical image data 1d (replicated medical image data) to be output next to a present piece of the medical image data 1d (replicated medical image data) that is being output on the monitor 12 in accordance with the sequence set in the setting information, and then outputs the searched-out piece of the medical image data 1d (replicated medical image data) onto the monitor 12. Alternatively, it can be a method by which the medical image data 1d (replicated medical image data) is automatically output onto the monitor 12 in accordance with a sequence set in the setting information without outputting the medical image-data list information 1c onto the monitor 12.

The components of each unit shown in the drawings in the above embodiments are conceptual for describing functions, and not necessarily to be physically configured as shown in the drawings (for example, FIGS. 2, 10, and 11). In other words, concrete forms of distribution and integration of the units are not limited to those shown in the drawings, and all or part of the units can be configured to be functionally or physically distributed and integrated in an arbitrary unit depending on various loads and conditions in use.

As described above, the image display method, the medical diagnostic imaging apparatus, and the medical image processing apparatus according to the embodiments of the present invention are useful for displaying medical image data, and suitable particularly for reducing a time until medical image data is displayed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display method, comprising:
replicating, by processing circuitry, a plurality of medical image data stored in a portable medium into a memory of a terminal device, in accordance with setting information in which a sequence of replicating a plurality of medical image data is predetermined;
starting to accept, by the processing circuitry, a selection of medical image data for displaying onto an output unit, upon starting of the replication in the replicating step;
determining, by the processing circuitry, whether or not the selected medical image data, selected in the starting step, has been replicated in the memory upon accepting the selection of the medical image data;
obtaining, by the processing circuitry, when it is determined that the selected medical image data has been replicated in the memory, the selected medical image data from the memory and when it is determined that the selected medical image data has not been replicated in the memory, the selected medical image data from the portable medium; and
displaying, by the processing circuitry, the obtained medical image data obtained in the obtaining step onto the output unit, wherein
the medical image data includes attribution information about a subject imaged into the medical image data, and
the replicating step includes replicating data except the attribution information about the subject among the medical image data.

2. The image display method according to claim 1, wherein
the determining step includes searching for replicated medical image data to be displayed subsequent to replicated medical image data being displayed onto the output unit, in accordance with the setting information, upon receiving a selection of medical image data for displaying, and
the displaying step includes displaying the obtained replicated medical image data onto the output unit.

3. The image display method according to claim 1, wherein the sequence is set based on at least one of a type of modality that collects the medical image data, an imaged site of the medical image data, and file numbers of the medical image data.

4. The image display method according to claim 1 further comprising:
reading, by the processing circuitry, the setting information in which a sequence of replicating a plurality of medical image data is set, from the portable medium.

5. An image display method, comprising:
replicating, by processing circuitry, a plurality of medical image data stored in a portable medium into a memory of a terminal device, in accordance with setting information in which a sequence of replicating a plurality of medical image data is predetermined;
starting to accept, by the processing circuitry, a selection of medical image data for displaying onto an output unit, upon starting of the replication in the replicating step;
determining, by the processing circuitry, whether or not the selected medical image data, selected in the starting step, has been replicated in the memory upon accepting the selection of the medical image data;
obtaining, by the processing circuitry, when it is determined that the selected medical image data has been replicated in the memory, the selected medical image data from the memory and when it is determined that the selected medical image data has not been replicated in the memory, the selected medical image data from the portable medium; and displaying, by the processing circuitry, the obtained medical image data obtained in the obtaining step onto the output unit, wherein the medical image data includes attribution information about a subject imaged into the medical image data, and identification information that uniquely identifies the medical image data, the replicating step includes replicating into the memory data except the attribution information about the subject among the medical image data, the determining step includes searching the portable medium by using the identification information included in the obtained replicated medical image data, and the displaying step includes displaying the attribution information about the subject, which is stored in association with the identification information, onto the output unit together with the obtained replicated medical image data.

6. An image display method, comprising:

replicating, by processing circuitry, a plurality of medical image data stored in a portable medium into a memory of a terminal device, in accordance with setting information in which a sequence of replicating a plurality of medical image data is predetermined;

starting to accept, by the processing circuitry, a selection of medical image data for displaying onto an output unit, upon starting of the replication in the replicating step;

determining, by the processing circuitry, whether or not the selected medical image data, selected in the starting step, has been replicated in the memory upon accepting the selection of the medical image data;

obtaining, by the processing circuitry, when it is determined that the selected medical image data has been replicated in the memory, the selected medical image data from the memory and when it is determined that the selected medical image data has not been replicated in the memory, the selected medical image data from the portable medium; and displaying, by the processing circuitry, the obtained medical image data obtained in the obtaining step onto the output unit, wherein the medical image data includes attribution information about a subject imaged into the medical image data, identification information that uniquely identifies the medical image data, and image attribution information for displaying the medical image data onto the output unit, the replicating step includes replicating into the memory data except the attribution information about the subject among the medical image data, the displaying step includes displaying the replicated medical image data obtained from the memory in the obtaining step onto the output unit in accordance with image attribution information included in the replicated medical image data, the determining step includes searching the attribute information about the subject from the portable medium by using the identification information included in the obtained replicated medical image data, and the displaying step includes displaying the attribution information about the subject, which is stored in association with the identification information, onto the output unit together with the obtained replicated medical image data.

7. A medical diagnostic imaging apparatus, comprising:
processing circuitry that
   takes a plurality of medical image data;
   writes the plurality of medical image data taken by the processing circuitry onto a portable medium;
   writes setting information in which a sequence of replicating the plurality of medical image data is set onto the portable medium; and
   writes onto the portable medium a computer program that causes a computer to execute, replicating the plurality of medical image data stored in the portable medium into a memory of a terminal device in accordance with the setting information, starting to accept a selection of medical image data for displaying onto an output unit upon starting of the replication in the replicating step, determining whether or not the selected medical image data, selected in the starting step, has been replicating in the memory, upon accepting the selection of the medical image data, obtaining, by the processing circuitry, when it is determined that the selected medical image data has been replicated in the memory, the selected medical image data from the memory and when it is determined that the selected medical image data has not replicated in the memory, the selected medical image data from the portable medium, and displaying the obtained medical image data onto the output unit, wherein the medical image data includes attribution information about a subject imaged into the medical image data, and the processing circuitry writes onto the portable medium a computer program that causes a computer to execute replicating data except the attribution information about the subject among the medical image data into the memory.

8. The medical diagnostic imaging apparatus according to claim 7, wherein the processing circuitry writes onto the portable medium a computer program that causes a computer to execute searching for replicated medical image data to be displayed subsequent to replicated medical image data being displayed onto the output unit in accordance with the setting information upon receiving a selection of medical image data for displaying, and then displaying the obtained replicated medical image data onto the output unit.

9. The medical diagnostic imaging apparatus according to claim 7, wherein the sequence is set based on at least one of a type of modality that collects the medical image data, an imaged site of the medical image data, and file numbers of the medical image data.

10. A medical diagnostic imaging apparatus, comprising:
processing circuitry that
   takes a plurality of medical image data;
   writes the plurality of medical image data taken by the processing circuitry onto a portable medium;
   writes setting information in which a sequence of replicating the plurality of medical image data is set onto the portable medium; and
   writes onto the portable medium a computer program that causes a computer to execute, replicating the plurality of medical image data stored in the portable medium into a memory of a terminal device in accordance with the setting information, starting to accept a selection of medical image data for displaying onto an output unit upon starting of the replication in the replicating step, determining whether or not the selected medical image data, selected in the starting step, has been replicating in the memory, upon accepting the selection of the medical image data, obtaining, by the processing circuitry, when it is determined that the selected medical image data has been replicated in the memory, the selected medical image data from the memory and when it is determined that the selected medical image data has not replicated in the memory, the selected medical image data from the portable medium, and displaying the obtained medical image data onto the output unit, wherein the medical image data includes attribution information about a subject imaged into the medical image data, and identification information that uniquely identifies the medical image data, and the processing circuitry writes onto the portable medium a computer program that causes a computer to execute replicating data except the attribution information about the subject among the medical image data into the memory, searching the portable medium by using the identification information included in the obtained replicated medical image data, and displaying the attribution information about the subject, which is stored in association with the identification information onto the output unit together with the obtained replicated medical image data.

11. A medical diagnostic imaging apparatus, comprising: processing circuitry that takes a plurality of medical image data;

writes the plurality of medical image data taken by the processing circuitry onto a portable medium:

writes setting information in which a sequence of replicating the plurality of medical image data is set onto the portable medium; and writes onto the portable medium a computer program that causes a computer to execute, replicating the plurality of medical image data stored in the portable medium into a memory of a terminal device in accordance with the setting information, starting to accept a selection of medical image data for displaying onto an output unit upon starting of the replication in the replicating step, determining whether or not the selected medical image data, selected in the starting step, has been replicating in the memory, upon accenting the selection of the medical image data, obtaining, by the processing circuitry, when it is determined that the selected medical image data has been replicated in the memory, the selected medical image data from the memory and when it is determined that the selected medical image data has not replicated in the memory, the selected medical image data from the portable medium, and displaying the obtained medical image data onto the output unit, wherein the medical image data includes attribution information about a subject imaged into the medical image data, identification information that uniquely identifies the medical image data, and image attribution information for displaying the medical image data onto the output unit, and the processing circuitry writes onto the portable medium a computer program that causes a computer to execute replicating data except the attribution information about the subject among the medical image data into the memory, displaying the replicated medical image data obtained from the memory in the obtaining step onto the output unit in accordance with image attribution information included in the replicated medical image data, searching the portable medium by using the identification information included in the obtained replicated medical image data, and displaying the attribution information about the subject, which is stored in association with the identification information, onto the output unit together with the obtained replicated medical image data.

12. A medical image processing apparatus, comprising: processing circuitry that writes a plurality of medical image data onto a portable medium;

writes setting information in which a sequence of replicating the plurality of medical image data is set onto the portable medium; and writes onto the portable medium a computer program that causes a computer to execute, replicating the plurality of medical image data stored in the portable medium into a memory of a terminal device in accordance with the setting information, starting to accept a selection of medical image data for displaying onto an output unit upon starting of the replication in the replicating step, determining whether or not the selected medical image data, selected in the starting step, has been replicating in the memory upon accepting the selection of the medical image data, obtaining, by the processing circuitry, when it is determined that the selected medical image data has been replicated in the memory, the selected medical image data from the memory and when it is determined that the selected medical image data has not replicated in the memory, the selected medical image data from the portable medium, and displaying the obtained medical image data onto the output unit, the medical image data includes attribution information about a subject imaged into the medical image data, and the processing circuitry writes onto the portable medium a computer program that causes a computer to execute replicating data except the attribution information about the subject among the medical image data into the memory.

13. The medical image processing apparatus according to claim 12, wherein the medical image data includes attribution information about a subject imaged into the medical image data, identification information that uniquely identifies the medical image data, and image attribution information for displaying the medical image data onto an output unit, and the processing circuitry writes onto the portable medium a computer program that causes a computer to execute replicating data except the attribution information about the subject among the medical image data into the memory, displaying the replicated medical image data obtained from the memory in the obtaining step onto the output unit in accordance with image attribution information included in the replicated medical image data, searching the portable medium by using the identification information included in the obtained replicated medical image data, and displaying the attribution information about the subject, which is stored in association with the identification information, onto the output unit together with the obtained replicated medical image data.

14. The medical image processing apparatus according to claim 12, wherein the processing circuitry writes onto the portable medium a computer program that causes a computer to execute searching for replicated medical image data to be displayed subsequent to replicated medical image data being displayed onto the output unit in accordance with the setting information upon receiving a selection of medical image data for displaying, and then displaying the obtained replicated medical image data onto the output unit.

15. The medical image processing apparatus according to claim 12, wherein the sequence is set based on at least one of a type of modality that collects the medical image data, an imaged site of the medical image data, and file numbers of the medical image data.

16. A medical image processing apparatus, comprising: processing circuitry that
writes a plurality of medical image data onto a portable medium;
writes setting information in which a sequence of replicating the plurality of medical image data is set onto the portable medium; and
writes onto the portable medium a computer program that causes a computer to execute, replicating the plurality of medical image data stored in the portable medium into a memory of a terminal device in accordance with the setting information, starting to accept a selection of medical image data for displaying onto an output unit upon starting of the replication in the replicating step, determining whether or not the selected medical image data, selected in the starting step, has been replicating in the memory upon accepting the selection of the medical image data, obtaining, by the processing circuitry, when it is determined that the selected medical image data has been replicated in the memory, the selected medical image data from the memory and when it is determined that the selected medical image data has not replicated in the memory, the selected medical image data from the portable medium, and displaying the obtained medical image data onto the output unit, wherein the medical image data includes attribution information about a subject imaged into the medical image data, and identification information that uniquely identifies the medical image data, and the processing circuitry writes onto the portable medium a computer program that causes a computer to execute replicating data except the attribution information about the subject among the medical image data into the memory, searching the portable medium by using the identification information included in the obtained replicated medical image data, and displaying the attribution information about the subject, which is stored in association with the identification information onto the output unit together with the obtained replicated medical image data.

* * * * *